United States Patent [19]
Gould et al.

[11] Patent Number: 5,620,845
[45] Date of Patent: Apr. 15, 1997

[54] IMMUNOASSAY DIAGNOSTIC KIT

[75] Inventors: Martin Gould, Gibbstown; Sudhakar Vulimiri, West Deptford, both of N.J.

[73] Assignee: Ampcor, Inc., Bridgeport, N.J.

[21] Appl. No.: 306,250

[22] Filed: Sep. 14, 1994

Related U.S. Application Data

[63] Continuation of Ser. No. 917,916, Jul. 21, 1992, abandoned, which is a continuation of Ser. No. 447,594, Dec. 8, 1989, abandoned, which is a continuation-in-part of Ser. No. 361,878, Jun. 6, 1988, abandoned.

[51] Int. Cl.⁶ .................. G01N 33/543; G01N 33/544; G01N 33/569
[52] U.S. Cl. .................. 435/5; 422/55; 422/56; 422/57; 435/7.1; 435/7.32; 435/7.94; 435/970; 435/971; 436/510; 436/518; 436/528; 436/529; 436/530; 436/531; 436/532; 436/810
[58] Field of Search .................. 422/50, 55, 56, 422/57, 61; 435/4, 5, 7.1, 7.6, 7.9, 21, 28, 960, 970, 971, 972, 975, 7.32, 7.94; 436/510, 518, 528, 532, 529, 530, 531, 65, 808, 810

[56] References Cited

U.S. PATENT DOCUMENTS

| | | |
|---|---|---|
| 3,011,874 | 12/1961 | Deutsch . |
| 3,615,222 | 10/1971 | Mead ............................ 436/500 |
| 3,715,192 | 2/1973 | Wenz et al. ..................... 422/56 |
| 4,016,043 | 4/1977 | Schuurs et al. .................. 435/5 |
| 4,039,652 | 8/1977 | Adams et al. ................... 436/505 |
| 4,061,468 | 12/1977 | L'ange et al. ................... 422/56 |
| 4,094,647 | 6/1978 | Deutsch ........................ 435/4 |
| 4,168,146 | 9/1979 | Grubb et al. ................... 315/5.26 |
| 4,200,690 | 4/1980 | Root et al. .................... 435/7.22 |
| 4,205,058 | 5/1980 | Wagner et al. .................. 436/500 |
| 4,235,601 | 11/1980 | Deutsch et al. ................. 436/514 |
| 4,243,749 | 1/1981 | Sadeh et al. ................... 435/7.92 |
| 4,299,916 | 11/1981 | Litman et al. .................. 435/6 |
| 4,305,924 | 12/1981 | Piasio et al. .................. 435/528 |
| 4,366,241 | 12/1982 | Tom et al. ..................... 435/7.91 |
| 4,373,932 | 2/1983 | Gribnau et al. ................. 436/501 |
| 4,376,110 | 3/1983 | David et al. ................... 435/5 |
| 4,391,904 | 7/1983 | Litman et al. .................. 435/7.91 |
| 4,424,279 | 1/1984 | Bohn et al. .................... 436/534 |
| 4,427,769 | 1/1984 | Adlercreutz et al. ............. 435/7.92 |
| 4,444,880 | 4/1984 | Tom ............................ 435/7.92 |
| 4,486,530 | 12/1984 | David et al. ................... 435/7.91 |
| 4,496,654 | 1/1985 | Katz et al. .................... 435/7.5 |
| 4,522,922 | 6/1985 | Carro et al. ................... 436/500 |
| 4,540,659 | 9/1985 | Litman et al. .................. 435/7 |
| 4,595,661 | 6/1986 | Cragle et al. .................. 436/534 |
| 4,612,281 | 9/1986 | Desmonts et al. ................ 435/7.22 |
| 4,613,567 | 9/1986 | Yasoshima et al. ............... 435/7 |
| 4,628,036 | 12/1986 | Scheepens et al. ............... 436/520 |
| 4,632,901 | 12/1986 | Valkirs et al. ................. 435/5 |
| 4,637,978 | 1/1987 | Dappen ......................... 435/11 |
| 4,639,419 | 1/1987 | Olson et al. ................... 435/5 |
| 4,657,869 | 4/1987 | Richards et al. ................ 435/287 |
| 4,659,678 | 4/1987 | Forrest et al. ................. 436/512 |
| 4,666,866 | 5/1987 | Krauth ......................... 436/518 |
| 4,668,619 | 5/1987 | Greenquist et al. .............. 435/7.7 |
| 4,673,657 | 6/1987 | Christian ...................... 436/501 |
| 4,698,298 | 10/1987 | Dedieu et al. .................. 435/7.93 |
| 4,703,017 | 10/1987 | Campbell et al. ................ 436/501 |
| 4,727,019 | 2/1988 | Valkirs et al. ................. 435/5 |
| 4,737,453 | 4/1988 | Primus ......................... 435/5 |
| 4,740,468 | 4/1988 | Weng et al. .................... 435/7.91 |
| 4,745,073 | 5/1988 | Forrest et al. ................. 436/518 |
| 4,774,177 | 9/1988 | Marks .......................... 435/7 |
| 4,786,589 | 11/1988 | Rounds ......................... 435/5 |
| 4,792,521 | 12/1988 | Shochat ........................ 435/7 |
| 4,803,170 | 2/1989 | Stanton et al. ................. 436/518 |
| 4,816,392 | 3/1989 | Hokama ......................... 435/7.21 |
| 4,818,677 | 4/1989 | Hay-Kaufman et al. ............. 435/4 |
| 4,822,565 | 4/1989 | Kohler ......................... 422/57 |
| 4,826,759 | 5/1989 | Guire et al. ................... 435/4 |
| 4,829,010 | 5/1989 | Chang .......................... 436/518 |
| 4,931,385 | 6/1990 | Block et al. ................... 435/7.94 |
| 4,962,023 | 10/1990 | Todd et al. .................... 435/7 |

FOREIGN PATENT DOCUMENTS 0250137   12/1987   European Pat. Off. .
2099578   12/1982   United Kingdom .

*Primary Examiner*—David Saunders
*Attorney, Agent, or Firm*—Norman E. Lehrer; Franklyn Schoenberg

[57] ABSTRACT

An immunoassay process is provided for the detection of a target antigen in a fluid sample where an admixture of the target antigen and a labeled capture reagent against the target antigen is contacted by a solid polymeric carrier having bound to a portion of its surface a capture reagent against the target antigen and visual determination of a change in color of the bound labeled reaction product on the surface of the solid carrier member serves to readily detect the presence of the target antigen.

20 Claims, 1 Drawing Sheet

U.S. Patent    Apr. 15, 1997    5,620,845
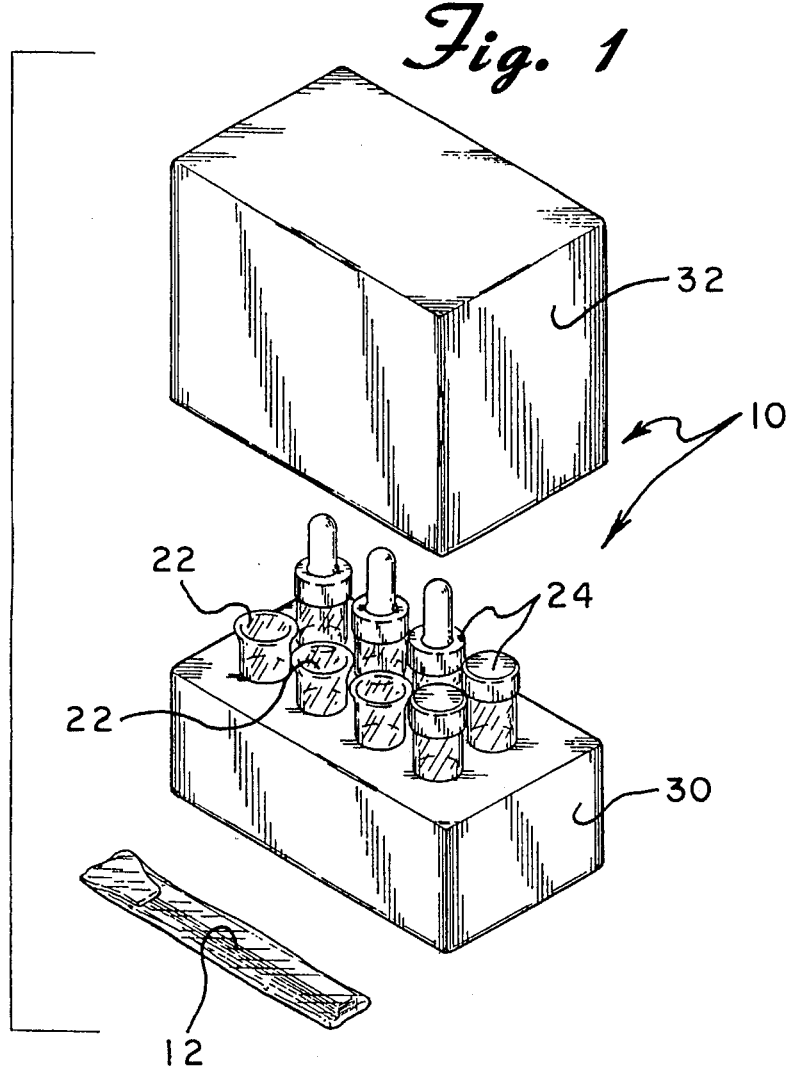
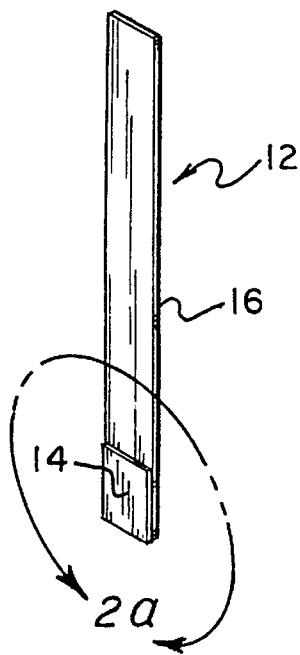
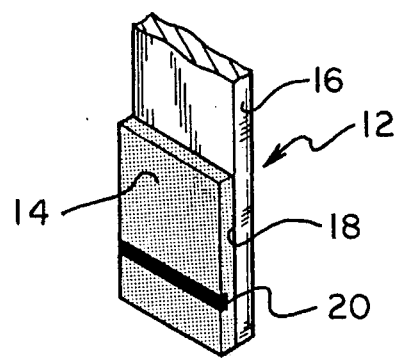

IMMUNOASSAY DIAGNOSTIC KIT

REFERENCE TO RELATED APPLICATION

This application is a continuation of application Ser. No. 07/917,916, filed Jul. 21, 1992 and now abandoned, which is a continuation of Ser. No. 07/447,594, filed Dec. 8,1989 and now abandoned, which is a continuation-in-part of Ser. No. 07/361,878, filed Jun. 6, 1988 and now abandoned.

FIELD OF THE INVENTION

The present invention relates to diagnostic devices and methods and, more particularly, to immunoassay diagnostic devices and methods for readily detecting and/or monitoring the presence of antigenic substances in fluids such as body fluids, culture media, food, water and the like.

BACKGROUND OF THE INVENTION

For a number of years, immunoassay procedures have replaced other procedures used for in vitro diagnostic methods to detect or quantitate a variety of antigens and/or antibodies in fluids and particularly body fluids such as blood serum or urine with important biologic or pharmacologic properties. The high levels of sensitivity and specificity achieved with immunoassays result from the specific, high-affinity, reversible binding of antigens to antibodies, and from the existence of methods for attachment of sensitive detectable labels (radioactive isotopes, fluorophores, ferritin, free radicals, bacteriophages and enzymes) to antibodies or antigens. Radioactive isotopes and enzymes are currently the most extensively used labels although the use of enzymes is generally preferred and the number of sensitive, specific immunoassays employing enzyme "tags" is expanding rapidly.

Immunoassay techniques are based upon the complex binding of the antigenic substance being assayed with an antibody or antibodies in which one or the other member of the complex may be labeled, permitting the detection and/or quantitative analysis of the target substance by virtue of the label activity associated with the labeled antigen complex or antibody. Immunoassays are generally classified into two groups: the heterogeneous immunoassay in which a labeled antigen or antibody is separated from the labeled antigen-antibody complex before measurement of label activity in either fraction; and the homogeneous immunoassay in which the activity of labeled antigen is measured in the presence of labeled antigen-antibody complex.

Two such diagnostic assay techniques used to determine the presence or amount of antigen in body fluids are generally known as "competitive" assays and "non-competitive or sandwich" assays. Typically, in "competitive" assay techniques, an unlabeled polyclonal antibody preparation bound to a solid support or carrier is first reacted with a labeled antigen reagent solution and then with the body fluid sample wherein the antigen in the sample competes with the labeled antigen for sites on the supported antibody. The amount of labeled antigen reagent displaced indicates the quantity of antigen present in the fluid sample to be detected.

In the case of a "sandwich" or "non-competitive" assay, a quantity of unlabeled polyclonal or monoclonal antibody bound to a solid-support or carrier surface, is reacted with a body fluid sample being evaluated for antigens, and then, after suitable incubation time and washing, the sample is further incubated with a solution of labeled antibody. The labeled antibody bound to the solid phase in an antibody-antigen-antibody sandwich or the amount of unbound labelled antibody in the liquid phase would be determined as a measure of the presence of antigen in the test sample.

The ready availability of monoclonal antibodies has made possible the modification of immunoassay procedures such as disclosed, for example, in U.S. Pat. Nos. 4,376,110 and 4,486,530 to David et al., wherein antibodies specific to antigens could be employed to detect such antigens in body fluids reducing or eliminating certain intermediate steps in the assay. Nonetheless, the processes heretofore typically employed require measured quantities of reagents and controlled extended reaction times as well as several washings and quenching, limiting these procedures to hospitals and laboratories where trained personnel and suitable equipment are available to perform the assays. Thus, the desirability of a relatively simple procedure and apparatus which made readily possible such assays in the physicians office or even their use by lay persons in home health care programs would be evident.

Over the years, many attempts have been made to develop more accurate, sensitive and definitive tests and devices for immunoassay diagnostic testing. For example, in U.S. Pat. No. 4,168,146 to Grubb et al., U.S. Pat. No. 4,200,690 to Root et al., and U.S. Pat. No. 4,373,932 to Gribnau et al., immunoassays are described for the detection of the presence of various antigens in body fluids and the like which employ reagents such as antibodies bound to a variety of porous support or carrier materials and dye labeled antibodies or the like. Such devices and methods, however, are generally directed to immunoassays for specific antigenic substances using particular types of porous carrier materials and labels for the antibody reagents which exhibit limited sensitivity and accuracy while requiring several operations including washing and/or quenching steps and extended periods for incubation which limit their suitability for use by less skilled personnel in a doctors office or home care situation.

More recently, there have been disclosed, for example, in U.S. Pat. Nos. 4,632,901 and 4,727,019 to Valkirs et al.; U.S. Pat. No. 4,639,419 to Olson et al.; U.S. Pat. No. 4,703,017 to Campbell et al.; and U.S. Pat. No. 4,786,589 to Rounds, procedures for conducting particular types of immunoassays in a relatively short period of time and routine fashion which employ generally simple apparatus. However, while such procedures and devices reduce the complexity and time for certain assays, several steps including a washing and/or quenching step are still generally necessary, the sensitivities thereof are limited and the test specimens are generally not suitable for extended periods of storage. Thus, even further simplification or efficacy would be desirable.

SUMMARY OF THE INVENTION

It is an object of the present invention to provide an apparatus for use in an immunoassay which is suitable for readily and accurately detecting and/or monitoring the presence of antigenic substance in liquids or fluids such as body fluids, culture media, food, water and the like without the need for multiple steps or washing.

It is another object of the present invention to provide an immunoassay diagnostic kit which employs a test strip or the like for detecting and/or monitoring the presence of antigenic substances in fluids such as body fluids and the like, which test strip can be employed by immersion in an assay and desired results can be obtained without the need for washing, quenching, multiple steps or extended delays.

It is a further object of the present invention to provide a test device such as a "dip-stick" type test strip which can be employed to visually detect and/or monitor the presence of antigenic substances in fluids such as body fluids and the like by immersion in an assay and can be retained as a record of such assay results.

It is a still further object of the present invention to provide a process for the immunoassay of fluids such as body fluids and the like for the detection and/or monitoring of antigenic substances which can be readily carried out in a physicians office or in home health care situations as well as in hospitals and clinical laboratories.

It is another object of the present invention to provide a process for the immunoassay of fluids such as body fluids and the like for the detection and/or monitoring of an antigenic substance which can be readily carried out in one or two steps with readily available equipment and wherein the results can be accurately determined visually by a test strip or similar device.

In accordance with the present invention there is provided a process for readily performing immunoassays which does not require any washing or quenching steps nor more than one or two reaction steps and/or lengthy incubation periods. The assay of the present invention comprises contacting a fluid test sample to be assayed, such as a body fluid, culture media, food, water and the like containing a target immunologically active agent, e.g., an antigen, with a labeled immunologically active reagent against said target antigen (labeled capture reagent), preferably an enzyme or the like labeled capture reagent to permit detection, and with an immunologically active reagent, such as an antibody reagent against said target antigen, bound to a portion of a solid carrier member (bound capture reagent), preferably, with the portion of supported solid carrier member not containing bound capture reagent being substantially blocked against binding to other immunologically active agents. In a preferred embodiment of the invention, the fluid test sample is admixed with a solution of labeled capture reagent against the target antigen followed by contacting the reaction admixture with the bound capture reagent. After a brief incubation, the reaction that has occurred is determined by visualization or measurement, preferably by detection of labeled capture reagent, as an indication of the presence of the target antigen in the fluid sample.

For example, an antigen present in the fluid test sample will bind to the labeled antibody capture reagent against the target antigen when the body fluid test sample is first admixed with the labeled antibody, and then upon contacting the admixture with the bound antibody capture reagent, the antigen also binds to available sites on such bound antibody to form an antibody-antigen-antibody "sandwich." In accordance with the invention, visual evaluation of the reaction that has occurred as an accurate indication of the presence of the target antigen in the sample can be readily achieved by detection of the presence of labeled antibody on the solid carrier member, surprisingly and unexpectedly, without the need for washing and/or quenching or extended periods of incubation. In the case of an enzyme labeled antibody capture reagent, for example, a solution of color forming substrate which reacts with the enzyme label will render a readily discernible visual color change to the labeled complex bound to the carrier member as the solution contacts the same. Such color forming substrate in encapsulated or other time-release form may be included in the body fluid-labeled antibody admixture or may be in a solution separate from the reaction mixture into which the supported complex can be immersed.

In another aspect of the invention, the apparatus of the invention comprises, as a first component, an insoluble solid carrier member to which is strongly bound over only a portion of one surface thereof a desired amount of a bound capture reagent against the target agent being assayed, such as an antibody against a target antigen, generally in a controlled linear, dot-like or other desired pattern, said carrier member preferably being affixed to the surface of a non-absorbent, inert support. Preferably, the portion of the carrier member not containing the bound capture reagent is substantially blocked against binding to other immunologically active agents. The apparatus further comprises, as a second component, at least one container which is non-absorbent and inert to immunologically active agents in which a fluid test sample and a labeled capture reagent may be admixed and which permits insertion of said first component into said admixture.

In the following specification and claims the term "antigen" designates all substances which, as such, or in form of a protein-complex, have antigenic activity, including high molecular weight proteinaceous components of human body liquids, hormones, bacteria, specific bound bacteria antigens, bacteria-produced toxins, virus etc., and lower molecular weight chemicals which react with a body protein to form a protein-complex with antigenic activity.

Antibodies are proteins which exhibit a specific immunological activity against the antigen which caused their formation. Antibodies are very similar in their overall protein-structure, but are distinguished from each other by their specific affinity to different antigens. In the following specification and claims the term "antibody" is meant to denote a proteinaceous material which exhibits antibody activity, that is, the antibody in substantially pure form or in form of a mixture having a high antibody-activity, e.g., an antiserum.

In the following specification and claims, the term "immunologically active agent" is meant to include antigens, antibodies and immunologically active binders.

Other objects and advantages of the present invention will become apparent from the detailed description thereof taken in conjunction with the drawings.

BRIEF DESCRIPTION OF THE DRAWINGS

For the purpose of illustrating the invention, there is shown in the accompanying drawing one form which is presently preferred; it being understood that the invention is not intended to be limited to the precise arrangements, and instrumentalities shown.

FIG. 1 is a perspective view of an immunoassay diagnostic kit in accordance with the invention; and FIG. 2 is a perspective view of a "dip stick" test device in accordance with the invention.

FIG. 2a is an enlarged perspective view, partly broken away, of the "dip stick" test device of FIG. 2.

DETAILED DESCRIPTION OF THE INVENTION

The apparatus of the present invention is useful in a variety of immunoassays for readily and accurately detecting and/or monitoring the presence of antigenic substances in fluids such as body fluids including blood serum, urine, etc.; culture media; food; water; and the like. The apparatus can be provided as a diagnostic kit to permit such assays to be conveniently and accurately performed in a physician's office or in home health care programs as well as in hospitals and reference and clinical laboratories.

Referring now to the drawings, where like reference numerals identify like parts, there is illustrated in FIGS. 1, 2 and 2a, the apparatus in accordance with the invention to perform immunoassays in the form of a "diagnostic kit" shown generally as 10. The "diagnostic kit" 10 comprises as a first component, a "dip-stick" type device or test strip 12 comprising a thin, insoluble, solid film-like carrier member 14 extending over and affixed to a portion of one surface of a non-adsorbent, inert support 16 by a suitable adhesive 18 and the like which is inert to immunologically active agents. Bound to a portion of the surface of the thin, carrier member 14 in a linear or any other desired pattern or array is a bound capture reagent 20, preferably a polyclonal or monoclonal antibody preparation or mixture thereof against the target antigen in a fluid test sample. Antibodies suitable for use in accordance with the invention may be prepared by any of the techniques known in the art.

Carrier member 14 can be prepared from any insoluble, solid material to which immunologically active agent preparations such as antibodies or antigens can be strongly attached by chemical binding and/or adsorption, and does not contain functional groups which will interfere with the immunological chemical reaction. Especially suitable are solid non-fibrous materials which will chemically bind with immunologically active capture reagents and into which such capture reagents will rapidly diffuse during the coating thereof and when contacted during diagnostic testing. Suitable materials include organic polymers which can be used with film forming, blow molding, and other conventional fabrication techniques such as polyethylene, polyamides, e.g., nylon, polypropylene, ethylene-propylene copolymers, polybutylenes and polystyrene. Other suitable materials include halogenated organic polymers such as polyvinyl chloride, polyvinylidene chloride and polytetrafluoroethylene; polyesters such as polyethylene terephthalate, polyacrylates and polymethyl-acrylates; cellulose and cellulose derivatives. Also suitable but not preferred are fibrous cellulose and cellulose derivatives and non-organic materials such as glass fibers.

Typically, film forming materials are advantageously used which contain carboxyl groups, or primary or secondary amide groups such as polyacrylamide, or which has amino group residues or into which such groups have been introduced by chemical means, such as nylon, or on which an amide group can be provided, such as polyacrylonitrile having a nitrile group which can be converted to an amide group by known methods.

The thickness and degree of porosity of carrier member 14 are not critical and can vary depending on the particular immunoassay for which the "dip-stick" type test strip and/or kit is intended. Typically, the solid carrier member is in a thin, preferably non-fibrous, film-like form, generally of 10 mils or less in thickness, having a pore size generally in the range of from about 0.01 micron to about 2 microns, and preferably from about 0.20 to about 0.50 microns, but carrier members of a thickness to about one-quarter inch and/or having a pore size up to about 100 microns may be employed in certain applications. In addition, the solid generally film-like carrier member 14 may be attached to the two opposing sides of support 16.

The capture reagent can be coupled to the carrier member 14 by any of the well known techniques, such as coupling antibodies, either polyclonal or monoclonal, directly by the well known glutaraldehyde or succinimide method. The amount of capture reagent that is attached to the solid film-like carrier member 14 is important but may vary depending on the effective amount required and the affinity thereof to the carrier member which, in turn, is dependent on the immunological reaction in question. Preferably, to enhance the sensitivity of the test and intensity of color formation for detection of the presence of the target antigen the bound capture reagent 20 will be applied to only a relatively small portion of one surface of the solid carrier member 14 in a controlled linear, dot-like or other desired pattern or array by jet-type atomizer "guns" and the like which apply a desired quantity of material in a concentrated narrow band or array, e.g, a concentration of about 2.5 micrograms of capture reagent per 5 mm of carrier member in a linear band width from about 0.1 mm to about 8 mm, preferably from about 1 mm to about 3 mm, across the full width of the carrier member, i.e., a band length of from about 0.08 mm to about 1.3 mm, preferably from about 0.5 mm to about 0.7 mm.

In accordance with the practice of the invention, one or more separate bands of capture reagent may be applied and bound to one surface of the solid carrier member 14, thus enabling the detection of one or more target antigens in a sample fluid, preferably by concurrent assays. Bound capture reagents against a variety of different target antigens may be separately bound to the carrier member to facilitate the assays of different target antigens in a fluid test sample with the sensitivity and accuracy of each assay being substantially similar. It would be evident that such concurrent assays, however, would not be suitable in the case where cross-reacting antigens or capture reagents are involved.

To further maximize color formation of the labeled reaction complex bound to the bound capture reagent on the carrier member and thus the sensitivity of the assay, a blocking agent is preferably applied to the solid carrier member after attachment of the bound capture reagent(s) thereto. The blocking agent is applied to the carrier member by immersion or the like technique in an amount sufficient to eliminate or significantly reduce the binding sites on the carrier member for other immunologically active agents that may otherwise be bound to the carrier member 14 during an assay. The suitability of blocking agents depend on the properties of the solid film-like carrier member with respect to the hydrophobicity and hydrophilicity thereof and their ability not only to block sites on the surface of the carrier member but to penetrate throughout the mass thereof. Exemplary suitable blocking agents include BSA, ethanolamine, ethylenediamine, aminoethanethiol, diaminehydroxypropane, aminopropanesulfonate, glucosamine dithiotreitol, 3-aminopentane; amino acids such as glycine, glutamate, lysine, cysteine; proteins such as gelatin and non-fat milk; animal serums such as bovine, rabbit, horse, rat and goat; casein and mixtures of the same. Mixtures of animals serum and casein are especially advantageous blocking agents.

In an advantageous embodiment, carrier members of the invention may also include a known or control concentration of the target antigen applied to a portion of one surface of said carrier by known techniques in a similar linear, dot-like or the like pattern employed for application of the bound capture reagent 20 to said carrier member but separate therefrom. The presence of such a control reagent on the film-like carrier member can serve as verification that the assay process of the invention was properly carried out as well as a further comparison for detection of the presence of the target antigen in the body fluid test sample.

Support 16 to which carrier member 14 is attached can be any non-absorbent polymeric and the like material which is inert to immunologically active agents and to which solid film-like carrier member 14 can be conveniently mounted.

The "diagnostic kit" 10 of the present includes as a second component, a vial 22 or the like container in which an admixture of immunologically active reagents can be reacted and permits insertion of a "dip-stick" type device or test strip 12 with the carrier member 14 in contact with the admixture. The vial 22 may be made of glass or a suitable plastic material which is inert to immunologically active agents and non-absorbent. The size of vial or container 22 is preferably selected so that prescribed amounts of a fluid test sample such as a body fluid and a labeled capture reagent such as a labeled antibody against target antigen in the test fluid may be admixed and reacted, and upon insertion therein of a carrier member 14 having bound antibody, intimate contact thereof with the reagent admixture will be effected. In general, the vial 22 is intended to be disposable after use and to facilitate the disposal of sample and reagents in a simple and hygienic fashion, it is preferred to include a suitable stopper for the vial 22 and/or envelope therefore (not shown) which can be of any known type.

As shown in the figures, additional vials 22 may be included with the kit 10 to facilitate detection of the presence of labeled capture reagent by contact with a color solution separate from the reaction mixture or to facilitate additional testing of the fluid test sample. In accordance with the invention, a "diagnostic kit" 10 may also include stoppered vials 24 and additional "dip-sticks" 12 containing stabilized immunologically active capture reagents to be used in various immunoassays such as disclosed in U.S. application Ser. No. 4,859,604 issued Aug. 27, 1989, the disclosure of which is incorporated by reference, color substrates for detection, standardized test samples for comparison testing and the like. As also shown in the figures, the kit 10 may be provided with a base stand 30 and cover therefore 32 to facilitate storage and shipping as well serving as a stand for the vials 22 when running the assays.

As noted hereinabove, in accordance with the practice of the invention the fluid test sample such as a body fluid, culture media, food, water and the like is admixed with a labeled capture reagent, for example, a monoclonal or polyclonal antibody to a target antigen in the test sample. In the case of an immunoassay, the labeled capture reagent binds to the target antigen in the test fluid during the reaction in the vial 22.

Preferably the labeled reagent is labeled with an enzyme although other conventional labels may be used in appropriate circumstances, such as, for example, a fluorescent label or a radioactive isotope. Useful labels also include microspheres loaded with a colored dye, microencapsulated or other time-release forms of colored dyes, or enzyme-dye conjugates. Other useful labels may be dyes from which conjugates with capture reagents such as an antibody may be prepared using known techniques. Useful in the preparation of such conjugates include dyes generally having functional amine groups such as Azure A, Azure B, Azure C, Methylene Blue, Thionin and the like as described in H. J. Conn, *BIOLOGICAL STAIN*, 9th Edition, 1977, Williams and Williams Co.

After the fluid test sample and labeled capture reagent have been admixed in vial 22, a solid film-like carrier member 14 as "dip-stick" 12 having bound capture reagent 20 such as an antibody against the target antigen, which, as indicated, can be a polyclonal or monoclonal antibody or mixture thereof, is immersed in the admixture in vial 22. If, as noted, the fluid test sample contains a target antigen and the labeled capture reagent in the admixture is a labeled antibody to the target antigen, the antigen and labeled antibody bind together. In this case, when the capture reagent bound to the solid film-like carrier member 14 is an antibody against the target antigen, the antigen in the labeled complex will also react with and bind to available sites on said bound antibody with the formation of an antibody-antigen-antibody "sandwich." Visual detection of the presence of target antigen in the fluid test sample can then be readily accomplished by visual color change after only a brief incubation period (about 1–5 minutes), which in the case of labeled antibody reagent occurs by virtue of the use, for example, of a solution of color forming substrate which reacts with the enzyme label as the solution contacts the same in the antibody-antigen-antibody "sandwich" bound to the carrier member. Such color forming substrate may be present in the admixture in time-release form or may be in a solution in a vial separate from the reaction mixture into which the complex bound to the carrier member can be immersed. In any case, there is no need to wash or treat the carrier member prior to contacting the color forming solution, and to further quenching of the reaction. The results as evidenced by the "dip-stick" can be retained as a permanent record.

As shown in FIG. 2a, the linear pattern 20 depicts the enhanced color development of the bound antibody (capture reagent) compared to the surrounding blocked portions of the carrier member achieved by virtue of the controlled application of said bound capture reagent. This makes readily discernible by visual detection the presence of labeled antibody and target antigen which are bound thereto. The color change results, as noted herein, from the use of any one of a variety of methods for detecting the label on the sandwich complex bound to the carrier member. As would be evident, detection of the presence of a target antigen by instrument measurement and the like of the labeled antibody bound to the solid carrier member would be an alternative method for practice of the present invention. As indicated, similar means may be employed for detecting the presence of more than one antigen in the test fluid by concurrent assays employing appropriate bound and labeled capture reagents against the target antigens.

In another embodiment, application of the invention may be carried out by inserting the "dip-stick" type device 12 with carrier member 14 having bound capture reagent 20 such as an antibody against the target antigen into vial 22 and adding a fluid test sample with a target immunologically active agent (antigen) and labeled antibody capture reagent against said target antigen into the vial 22 for contact with the carrier member 14. While the order of addition of the fluid test sample and labeled capture reagent to the vial or container 22 is not critical, it is generally preferred to add the test sample first.

The apparatus of this invention may also be used to perform competitive assays, i.e., assays in which the capture reagent bound to the solid carrier member mounted on the "dip-stick" type device 12 and for which the target immunologically active agent (antigenic substance) in the fluid test sample competes with a fixed quantity of labeled capture reagent added to the fluid test sample or added following sample addition.

The foregoing is a general description of the apparatus and process of the invention, primarily in its use in performing immunoassays which readily provides accurate detection of target antigens in fluid test samples in a short time, e.g., about five to ten minutes. The process can be carried out in one or possibly two simple steps and can be readily performed in home care situations or in hospitals. The invention will now be demonstrated by the description of certain specific examples of its practice. In these examples, unless stated otherwise, all temperatures are centigrade and all parts and percentages are by weight.

EXAMPLE 1

An antibody against human chorionic gonadotropin (HCG), an antigen which is elevated in the urine of pregnant women, is bound in a linear pattern to a film-like carrier member mounted on a dip-stick device such as 12 in the Figures.

Samples of urine are admixed in a vial 22 with an antibody against HCG to which is bound alkaline phosphatase. After a brief period, the dip-stick device 12 is inserted into the reaction mixture, and then after a further brief period of incubation, i.e. one to five minutes, the dip-stick is inserted into another vial containing a dye solution composed of a mixture of 0.7 grams per liter of 5-Bromo-4-Chloro-3-Indolye Phosphate and 0.20 grams per liter of Nitro Blue Tetrazolium Chloride. A line that is placed on the film-like carrier member by bound antibody will become visible as a distinct blue color if the target antigen is present within the detection range of the test within a short time, i.e. one to five minutes.

EXAMPLE 2

In this test for detection of the presence of human chorionic gonadotropin (HCG), an antigen which is elevated in urine and blood serum of pregnant women, a dip-stick device with a thin nylon film carrier member is used. The carrier member contains two spaced reaction zones, a positive control zone to which is bound a narrow linear band (1 mm to 3 mm wide) of HCG equivalent to 50 mIU/ml HCG and a specimen reaction zone to which is bound a narrow linear band (1 mm to 3 mm wide) of a polyclonal antibody (sheep) against beta-HCG (infinity purified) at a concentration of 2.5 microgram of antibody per 5 mm of carrier. The bands of reagents are applied to the carrier surface with a TLC spotter device. After the reagents dry, the carrier member is immersed in a goat serum for three to five minutes followed by immersion in a solution of casein (Hammarsten casein from BDH Chemicals Ltd., Poole, England) and then immersion in a 1% mannitol solution.

Samples of centrifuged blood serum are admixed with a monoclonal antibody (anti-HCG mouse) to which is bound alkaline phosphatase in sample test vials at room temperature for a short time (about one minute) after which the dip-stick devices are inserted into the reaction admixture in the test vials and permitted to incubate for four to five minutes. The dip-sticks are then placed in a dye solution composed of 0.4 g/l of Nitro Blue Tetrazolium and 1.6 g/l of 5-Bromo-4-Chloro-3-Indolyl Phosphate for five minutes. The reaction zone linear band placed on the carrier member of the dip-stick will become visible as a distinct blue color if the antigen is present in the sample fluid. The control zone linear band placed on the carrier member will become visible as a distinct blue color of generally similar color intensity to the reaction zone color depending on the antigen concentration in the fluid test sample. No washing or quenching is required to achieve the desired results and the dipsticks can be retained for permanent record purposes.

Although assays for HCG as an antigen have been described, it will be appreciated that a similar assay for other antigens may be employed in accordance with the invention. Other such antigens that may be assayed include Salmonella, Epstein Barr, Chlamydia, Lyme disease, *Escherichia coli*, Proteus, Klebsiella, Staphylococcus, Pseudomonas, *Clostridium difficile*, hepatitis A and B, human immunodeficiency virus (HIV), Equine pregnancy, Canine heartworm, Feline leukemia etc. If a label other than an enzyme or color development materials other than dye solutions are used, the procedure may be varied, but these and other such variations by persons skilled in the art may be made without departure from the spirit of the invention. Furthermore, while the invention has been described as being applicable to the medical field for detecting the presence of substances in various fluids such as body fluids, it should be understood that, as indicated, it is also useful in other fields such as detecting substances in food products, in the environment, etc.

What is claimed is:

1. An immunoassay process for the detection of a target immunologically active agent in a liquid sample comprising:
   a) contacting said liquid sample containing said target immunologically active agent to be assayed with a labeled capture reagent against said target immunologically active agent, and with a controlled effective amount of a bound capture reagent against said target immunologically active agent bound to a solid carrier member over only a portion thereof in a controlled substantially specific array and wherein the remaining portion of said solid carrier member having been treated with animal serum and with a solution of a casein protein in an effective amount is substantially blocked against bonding to said labeled capture reagent and said target immunologically active agent; and
   b) detecting the presence of said target immunologically active agent by determining the label bound to said bound capture reagent on said solid carrier member as an indication of the presence of the target immunologically active agent in said fluid sample.

2. The immunoassay process according to claim 1, wherein the presence of target immunologically active agent is detected without washing the solid carrier member.

3. The process according to claim 2, wherein said target immunologically active agent is an antigen.

4. The process according to claim 3, wherein said labeled capture reagent is an enzyme labeled antibody against said target antigen.

5. The immunoassay process according to claim 3, wherein said solid carrier member is a film of non-fibrous material and said bound capture reagent is applied to and bound over only a portion of one surface of said solid carrier member by jet-type atomizer means in a controlled narrow linear band containing a controlled amount of said bound capture reagent.

6. The immunoassay process according to claim 5, wherein said solid carrier member is a polymeric material to which said bound capture reagent is bound.

7. The immunoassay process according to claim 6, wherein said bound capture reagent consists essentially of an immobilized antibody against said target immunologically active agent and said labeled capture reagent is an antibody reagent against said target immunologically active agent to which is attached a label.

8. The process according to claim 2, wherein said labeled capture reagent and said bound capture reagent are monoclonal or polyclonal antibodies or mixtures thereof.

9. The process according to claim 2, wherein said liquid sample is a body fluid, culture media, food or water.

10. The process according to claim 1, wherein said labeled capture reagent is an enzyme labeled antibody and the determining label step comprises contacting said solid carrier member with a color forming solution selected to generate a color change of the enzyme label which is visual.

11. The process according to claim 10, wherein said color forming solution is in a time-release form in an admixture of said fluid sample of target immunologically active agent and said labeled capture reagent.

12. An immunoassay process for the detection of a target immunologically active agent in a liquid sample consisting essentially of admixing said liquid sample containing said target immunologically active agent with a labeled capture reagent against said target immunologically reactive agent, contacting said admixture with a controlled effective amount of a bound capture reagent against said target immunologically active agent, said bound capture reagent being applied to and bound to a solid carrier member by jet-type atomizer means over only one surface thereof in a controlled substantially specific array and wherein the remaining portion of said solid carrier member is substantially blocked against bonding to said labeled capture reagent and said target immunologically reactive agent, and then contacting said bound capture reagent without washing the same with a color forming solution selected for detecting the presence of the target immunologically active agent by determining by visualization an indication of the presence of label bound to said bound capture reagent on said carrier member.

13. The immunoassay process according to claim 12, wherein said target immunologically active agent is an antigen.

14. The immunoassay process according to claim 13, wherein said solid carrier member is a polymeric material to which said bound capture reagent is bound and wherein the remaining portion of said solid carrier member is treated with animal serum and with a solution of a casein protein in an effective amount to substantially block the same.

15. The immunoassay process according to claim 14, wherein said bound capture reagent consists essentially of an immobilized antibody reagent against said target immunologically active agent and said labeled capture reagent is an antibody reagent against said target immunologically active agent to which is attached a label.

16. The immunoassay process according to claim 15, wherein said solid carrier member is a thin film of non-fibrous polymeric material to which said bound capture reagent is bound in a controlled linear or dot-like pattern consisting essentially of a controlled effective amount of said bound capture reagent.

17. The immunoassay process according to claim 16, wherein said bound capture reagent is chemically and/or absorptively bound to said carrier member.

18. The immunoassay process according to claim 16, wherein said labeled antibody reagent is an enzyme labeled antibody reagent.

19. The immunoassay process according to claim 13, wherein said antigen is selected from the group consisting of chorigonadotropin, Salmonella, Epstein-Barr, Chlamydia, an antigen of Lyme disease, *Escherichia coli*, Proteus, Kiebsiella, Staphylococcus, Pseudomonas and Hepatitis A & B.

20. The immunoassay process according to claim 12, wherein said solid carrier member is removed from contact with said reaction admixture and is directly placed in contact with said color-forming solution in a separate container without washing.

* * * * *